United States Patent
Rustick

(10) Patent No.: US 10,596,378 B2
(45) Date of Patent: Mar. 24, 2020

(54) METHOD FOR TREATMENT OF DEPRESSION USING SYNAPTIC PATHWAY TRAINING

(71) Applicant: Joseph Rustick, Phoenix, AZ (US)

(72) Inventor: Joseph Rustick, Phoenix, AZ (US)

( * ) Notice: Subject to any disclaimer, the term of this patent is extended or adjusted under 35 U.S.C. 154(b) by 232 days.

(21) Appl. No.: 15/787,526

(22) Filed: Oct. 18, 2017

(65) Prior Publication Data

US 2018/0104490 A1  Apr. 19, 2018

Related U.S. Application Data

(60) Provisional application No. 62/409,753, filed on Oct. 18, 2016.

(51) Int. Cl.
| | | |
|---|---|---|
| *A61N 1/36* | (2006.01) | |
| *A61N 1/04* | (2006.01) | |
| *A61K 31/135* | (2006.01) | |
| *A61K 31/451* | (2006.01) | |
| *A61K 31/48* | (2006.01) | |

(52) U.S. Cl.
CPC ....... *A61N 1/36082* (2013.01); *A61N 1/0456* (2013.01); *A61N 1/36025* (2013.01); *A61N 1/36034* (2017.08); *A61N 1/36178* (2013.01); *A61N 1/36185* (2013.01); *A61K 31/135* (2013.01); *A61K 31/451* (2013.01); *A61K 31/48* (2013.01)

(58) Field of Classification Search
None
See application file for complete search history.

(56) References Cited

U.S. PATENT DOCUMENTS 8,676,330 B2 * 3/2014 Simon ................ A61N 1/36021
607/46
9,649,501 B2 * 5/2017 Best ................... A61N 1/36025
(Continued)

FOREIGN PATENT DOCUMENTS

WO WO-2015069632 A1 * 5/2015 ............. A61B 3/112

OTHER PUBLICATIONS

Ronald S. Duman and George K. Aghajanian, Synaptic Dysfunction in Depression: Potential Therapeutic Targets, HHS Public Access, May 8, 2015, pp. 1-11, Science, New Haven CT.
(Continued)

*Primary Examiner* — Brian T Gedeon
(74) *Attorney, Agent, or Firm* — Schmeiser, Olsen & Watts LLP

(57) ABSTRACT

Disclosed are methods of treating depression, mania, post-traumatic stress disorder (PTSD), and various other neurologic conditions using synaptic pathway training. Methods of synaptic pathway training include, generally, achieving a favorable treatment result by activating a synaptic pathway using a pharmacologic agent, such as treating refractory symptoms of depression with ketamine, following by potentiation of the favorable result by repeatedly stimulating the activated pathway. Stimulation of a synaptic pathway may be achieved by intrinsic means, such as performance of cognitive exercised, or extrinsic means, such as by delivery of a sensory stimulus to the patient, placing a potential voltage difference across the brain or a brain region, or by placing the brain or a brain region in a magnetic field.

20 Claims, 3 Drawing Sheets

(56) References Cited

U.S. PATENT DOCUMENTS

| | | | | |
|---|---|---|---|---|
| 10,123,737 B2* | 11/2018 | Iacoviello | ............... | A61B 5/00 |
| 10,238,862 B2* | 3/2019 | Cook | ................... | A61N 1/3606 |
| 2011/0224571 A1* | 9/2011 | Pascual-Leone | .... | A61B 5/0484 |
| | | | | 600/544 |
| 2016/0005320 A1* | 1/2016 | deCharms | ............. | G09B 5/065 |
| | | | | 434/236 |

OTHER PUBLICATIONS

Adriana Feder, MD, et al., Efficacy of Intravenous Ketamine for Treatment of Chronic Posttraumatic Stress Disorder, JAMA Psychiatry, Jun. 2014, pp. 681-688, vol. 71, No. 6, American Medical Association.

Keith G. Rasmussen, et al., Serial Infusions of Low-Dose Ketamine for Major Depression, Journal of Psychopharmacology 27:5, pp. 444-450, SAGE (2013).

Carlos A. Zarate Jr., MD, et al., Replication of Ketamine's Antidepressant Efficacy in Bipolar Depression: A Randomized Controlled Add-on Trial, NIH Public Access, Jun. 1, 2013, pp. 1-18, Bethesda, Maryland.

* cited by examiner

METHOD FOR TREATMENT OF DEPRESSION USING SYNAPTIC PATHWAY TRAINING

CROSS REFERENCE TO RELATED APPLICATION

This application claims priority to United States (Provisional) Patent Application to Joseph Rustick, entitled "DEPRESSION TREATMENT," application No. 62/409,753, filed Oct. 18, 2016, now pending, the disclosure of which is hereby incorporated entirely herein by reference.

BACKGROUND OF THE INVENTION

Technical Field

This invention relates to methods for the treatment of a neurologic condition. In particular, the invention relates to methods of treating depression, mania, and post-traumatic stress disorder by training synaptic pathways in the brain.

State of the Art

Depression is common, and a significant public health problem in the United States. It is estimated that one in ten persons in the U.S. suffer from clinical depression.

Persons suffering from depression may experience a constellation of debilitating symptoms, including a lack of interest and pleasure in daily activities, significant weight loss or gain, insomnia or excessive sleeping, lack of energy, inability to concentrate, feelings of worthlessness, excessive guilt, and recurrent thoughts of death or suicide. Depression can occur as a primary mental health disorder, or may arise secondary to an unrelated primary illness.

Available treatments for depression include cognitive behavioral therapy (CBT), medications, and electroconvulsive therapy (ECT). CBT is effective in many cases, particularly when symptoms are mild to moderate and of recent onset, but less so in chronic or severe depression. CBT has been shown to be more effective with combined with medications, and vise-versa. Treatment of depression with medications is generally safe, however, onset of a therapeutic effect is gradual and may take at least several weeks to manifest, with maximal improvement seen only after eight weeks. If medications are discontinued, the symptoms generally return, often necessitating lifetime pharmacologic therapy. Moreover, medications, CBT, or combined CBT and medications are only effective in sixty to seventy percent (60%-70%) of cases. ECT is useful in up to ninety percent (90%) of patients and immediately effective, however, ECT can be associated with significant side effects, including effects on memory and cognitive impairment. Only about twenty percent (20%) of those with depression receive any treatment, and a significant percentage of those who are treated do not achieve significant or lasting improvement.

Currently available treatments for depression, therefore, are 1) effective only in a subset of patients; and 2) relatively short-lived.

Accordingly, what is needed is a safe and rapid-onset means for treating depression that is widely efficacious and which provides relief of symptoms over an extended period of time.

DISCLOSURE OF EMBODIMENTS OF THE INVENTION

Embodiments of the present invention include methods for treatment of a neurologic condition by synaptic training. The foregoing and other features and advantages of the invention will be apparent to those of ordinary skill in the art from the following more particular description of the invention and the accompanying drawings.

Disclosed is a method of treating a neurologic condition by synaptic pathway training comprising steps of activating a synaptic pathway with a pharmacologic agent; and stimulating the activated synaptic pathway.

In some embodiments, the pharmacologic agent comprises an N-methyl-D-aspartate receptor antagonist. In some embodiments, the pharmacologic agent comprises ketamine. In some embodiments, the pharmacologic agent is a member selected from the group of pharmacologic agents consisting of scopolamine, Namenda, dextromethorphan, amantadine, dextropropoxyphene, and ketobemidone.

In some embodiments, the pharmacologic agent is psilocybin. In some embodiments, the pharmacologic agent is phencyclidine. In some embodiments, the pharmacologic agent is lysergic acid diethylamide.

In some embodiments, the neurologic condition is depression. In some embodiments, the neurologic condition is bipolar disorder. In some embodiments, the neurologic condition is post-traumatic stress disorder.

In some embodiments, stimulating the synaptic pathway comprises performance of a cognitive training exercise. In some embodiments, the stimulating step comprises exposure of a person to a sensory stimulus. In some embodiments, the stimulating step comprises applying a magnetic field to a region of a brain. In some embodiments, the stimulating step comprises applying a potential voltage difference to a region of a brain. In some embodiments, the stimulating step comprises providing an auditory stimulus. In some embodiments, the stimulating step comprises providing a visible-wavelength light stimulus.

Disclosed is a method of enhancing treatment of a neurologic condition comprising steps treating the condition with a pharmacologic agent to alter a synaptic pathway; and extending a treatment result by repeatedly activating the synaptic pathway with a neural stimulating means.

In some embodiments, activating the synaptic pathway comprises performance of a cognitive training exercise. In some embodiments, activating the synaptic pathway comprises providing an external source of stimulation. In some embodiments, the external source is a magnetic field, a potential voltage difference, or an auditory stimulus.

Disclosed is a method of treating a neurologic condition by synaptic pathway training comprising steps activating a synaptic pathway by administering at least one dose of ketamine, at least 0.5 mg/kg; and stimulating the activated synaptic pathway by performing a cognitive exercise for at least thirty (30) minutes daily.

In some embodiments, the neurologic condition is depression, mania, or post-traumatic stress disorder.

DETAILED DESCRIPTION OF EMBODIMENTS OF THE INVENTION

Figure 1:
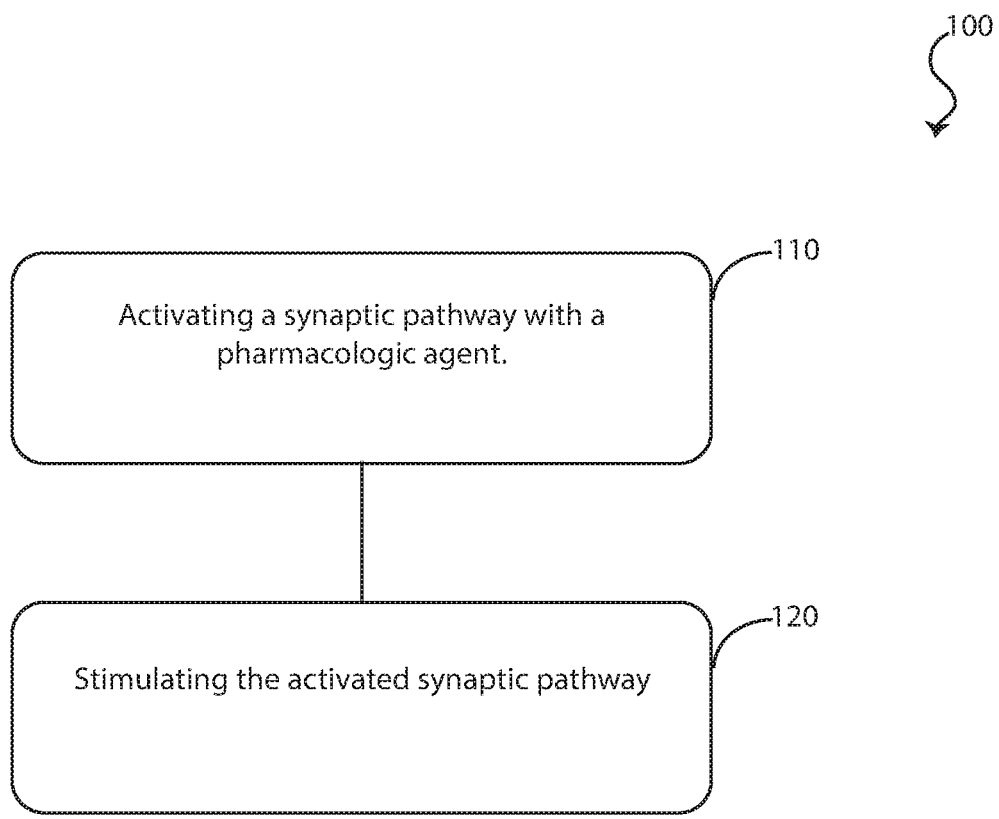
FIG. 1 is a flowchart showing steps of a method for treating a neurologic condition using synaptic pathway training.

As mentioned herein above, the disclosed invention relates to methods for the treatment of a neurologic condition. In particular, the invention relates to methods of treating depression, mania, post-traumatic stress disorder, and other neurologic conditions by training synaptic pathways in the brain.

As used herein, the following terms are intended to have a meaning as defined below, unless otherwise indicated.

"Synaptic density" means the number of synapses per unit volume of neural tissue, including brain tissue.

"Synaptic pathway" is used to describe a micro-anatomic pathway communicating a neural impulse between two neurons, wherein the two neurons form a focal anatomic association with one another. The synaptic pathway includes a presynaptic neuron, the anatomic association comprising a synapse, and a postsynaptic neuron.

"Pharmacologic agent" means a biologically active substance delivered to the body with the intent to render a therapeutic effect on a tissue or organ. Pharmacologic agents include any recognized drug and any substance used or acting as a drug.

"Stimulating" means delivering a physiologic provocation with the intent to activate a synapse.

"Cognitive training exercises" means an activity relating to or involving conscious intellectual activity, including but not limited to thinking, reasoning, or remembering.

Chronic or recurrent depression leads to neuroanatomic changes in the brain. Noninvasive brain imaging studies, such as computed tomography and magnetic resonance imaging (MRI), demonstrate volume loss in the hippocampus of patients with chronic or chronically recurring depression. Functional magnetic resonance imaging has been used to show micro-changes in blood flow within multiple regions of the brain in persons suffering from depression. These regions include the hippocampus, areas within the prefrontal cortex, basal ganglia, and limbic system. A corresponding decrease in synaptic density is also seen in these areas of depressed persons.

As discussed herein, currently available treatments for depression include CBT, pharmacologic agents, and ECT. The mechanism of action of antidepressant medications is incompletely understood, however, it is widely believed to involve manipulating levels of neurotransmitters; namely, serotonin, norepinephrine, and dopamine. CBT affects the brain by activating neurons, which increases the number of synapses (synaptic density) in some brain areas, including the hippocampus, in some patients. ECT does not "activate" neurons; rather, ECT causes a simultaneous depolarizing a broad area of brain tissue, and induces seizure activity which spreads neuronal depolarization. And although certain of these therapies may be effective in an individual patient, the beneficial effects of the therapy are typically short-lived, disappearing soon after the therapy is discontinued.

The methods described herein combine pharmacologic and stimulation therapies to achieve a surprising result—temporary improvements in mood and behavior experienced following initial treatment with a pharmacologic agent are made long-lasting by adding stimulation therapy. This combination treatment has been named "synaptic pathway training" because the method "trains" a group of synaptic pathways activated by an initial treatment to continue functioning in the desired way by using regular and repeating neurologic stimulation.

A non-limiting but representative example of such a method is provided. Ketamine is a N-methyl-D-aspartate (NMDA) receptor antagonist with opioid receptor activity. The structure of ketamine comprises an aryl cyclohexylamine. When administered in moderate doses, ketamine acts as a dissociative anesthetic. As an anesthetic, ketamine is rapid acting and has a short duration of action. Because moderate doses do not typically produce decreases in respiration or blood pressure, ketamine is useful in providing anesthesia in children and in various non-hospital settings. Ketamine may be parenterally administered using an intravenous, intramuscular, or trans-nasal route.

Administration of ketamine by intravenous infusion at a dose of about 0.5 milligrams per kilogram of patient body weight (mg/kg) over between about forty-five (45) and about sixty (60) minutes is used to produce relief of symptoms of depression. Higher doses may be used, although doses of about 1.0 mg/kg intravenously over 45 to 60 minutes produces a state of sedation with vivid visual sensory changes. Patients who experience these vivid visual sensory changes, however, experience a stronger anti depressive effect of the treatment. Administration of single-dose intravenous ketamine infusions is also associated with a transient increase in hippocampal volume corresponding with an increase in synaptic density. It is thought that that the increase in hippocampal volume and synaptic density resulting from the administration of single-dose ketamine allows non-depressive thought patterns to occur.

The anti-depressant effects of ketamine persist from about seven (7) to about twenty-one (21) days, after which symptoms of depression begin to re-emerge. If a second dose of ketamine is given by intravenous infusion six (6) days after the first dose, symptoms of depression do not return until approximately twenty-eight (28) days after the second treatment. Treating depression with two doses of intravenous ketamine six days apart, therefore, may result in approximately thirty-four (34) days of symptom relief.

Stimulation targeting the associated neural synaptic pathways activated by the ketamine, however, results in a profound prolongation of symptom relief. Stimulation may be intrinsic, extrinsic, or a combination of both. "Intrinsic stimulation" is stimulation delivered to the synaptic pathway by the patient engaging in active cognition, whereas "extrinsic stimulation" is the application of an external stimulus, the effects of which passively activate the synaptic pathway without any conscious participation by the patient. With delivery of either an active cognitive or passive sensory stimulus to the activated synaptic pathway, given repeatedly over an extended period of time, relief of symptoms of depression can be extended for between four to twelve months.

For example, one patient with chronic depression as a component of bipolar disorder underwent unsuccessful treatment with conventional antidepressant medications and CBT. Following this unsuccessful first-line therapy, multiple treatments with intravenous ketamine resulted in good relief from the depression, but the longest period of relief lasted only approximately twenty-eight (28) days. In an effort to prolong the results of treatment, synaptic training using cognitive activities ("brain HQ exercises") (an intrinsic stimulus) was undertaken for a single session of thirty-minutes each day.

Augmenting the ketamine infusions with synaptic training in this patient resulted in the obliteration of depressive symptoms for greater than one year. Symptoms of mania were also not experienced. The patient characterized the first four-month period starting with the first ketamine dose as feeling the best. The second four-month period, the patient felt "good," but not as well as during the first four-month period. During the third four-month period, the patient still felt much, much better than baseline (prior to ketamine treatment), although was subjectively looking forward to receiving an additional ketamine dose sometime in the future.

A novel aspect of this method is using a pharmacologic agent in combination with a neural stimulation means, whether extrinsic or intrinsic, to subsequently target the brain area (synaptic pathway) activated by the pharmacologic agent. It is should be noted that the use of many other pharmacologic agents other than ketamine may be used, depending on the synaptic pathway to be activated and the neurologic condition to be treated. It should also be noted that use many different means of targeted stimulation of the activated synaptic pathway are also contemplated. It should additionally be noted that many neurologic conditions other than depression may be treated with a combination of pharmacologic synaptic pathway activation following by training the activated synaptic pathway with repeated targeted stimulation.

The result of combining pharmacologic activation with targeted stimulation of the activated synaptic pathway is an increase in the efficacy and duration of effect of the treatment much, much longer than with the use of drug therapy or directed synaptic pathway stimulation alone. The exact mechanism of this effect is unknown; however, it is thought that the pharmacologic activation of a synaptic pathway in the brain, resulting in growth of new synapses between the neurons in the pathway, is made durable by "training" the synaptic pathway by regular and repeated stimulation of the pathway's presynaptic neuron.

FIG. 1 is a flowchart showing steps of a method for treating a neurologic condition using synaptic pathway training. In some embodiments, the neurologic condition is depression. "Depression" means either clinical diagnosis of either unipolar or bipolar depression. It should be understood, however, that treatment of many other neurologic conditions using method 100 is contemplated, including mental health conditions such as mania, post-traumatic stress disorder ("PTSD"), schizophrenia, dysthymia, chronic pain syndromes including complex regional pain syndrome, substance abuse disorders, neuropathic pain, dysesthesia, traumatic brain injury, and other neurologic illnesses and conditions.

FIG. 1 shows a method 100 comprising an activating step 110 and a stimulating step 120.

Activating step 110, in some embodiments, comprises activating a synaptic pathway with a pharmacologic agent. In some embodiments, the pharmacologic agent comprises an N-methyl-D-aspartate (NMDA) receptor antagonist. For example, as discussed herein, ketamine is an NMDA receptor antagonist used to activate various synaptic pathways associated with relieving symptoms and physical signs depression. Ketamine, other NMDA receptor antagonists, and other pharmacologic agents also activate synaptic pathways of many other neurologic conditions, including but not limited to conditions noted herein above. The pharmacologic agent, in some embodiments, is used to activate synaptic pathways to treat any of these aforementioned of other neurologic conditions.

In some embodiments, the pharmacologic agent is a serotonin receptor agonist, such as psilocybin, for example. In some embodiments, the pharmacologic agent is a muscarinic receptor agonist, such as scopolamine, for example.

Ketamine is administered at a standard dose of about 0.5 milligrams per kilogram body weight ("mg/kg") as an intravenous infusion, in some embodiments. In some embodiments, the dose of intravenous ketamine is about 1.0 mg/kg. In some embodiments, the dose of intravenous ketamine is between about 0.5 mg/kg and about 1.0 mg/kg.

A relief of symptoms of depression indicates activation of the synaptic pathways targeted for training. "Activation" of the synaptic pathway means an increase in the absolute number of functioning synaptic connections between axonal terminals of a presynaptic neuron and dendrites or cell bodies of one or more postsynaptic neurons. In some embodiments, the synaptic pathway is a prefrontal cortex synaptic pathway. In some embodiments, the synaptic pathway is a hippocampal synaptic pathway. In some embodiments, the synaptic pathway is a limbic system synaptic pathway.

The pharmacologic agent, like ketamine, for example, causes an increase in synaptic density between the presynaptic and postsynaptic neurons of the synaptic pathway which correlates to relief from symptoms of depression, or some other neurologic condition. As noted herein, some patients experience a relief of depressive symptoms following one dose of intravenous ketamine. Some patients, however, do not experience a relief of depression until receiving two doses of intravenous ketamine administered six (6) days apart. Some patients require greater than two intravenous ketamine doses, each dose following the preceding dose by a period of six days. Consequently, in some embodiments, activating step 110 comprises administering two doses of the pharmacologic agent. In some embodiments, activating step 110 comprises administering three doses of the pharmacologic agent. In some embodiments, activating step 110 comprises administering greater than three doses of the pharmacologic agent.

Stimulating step 120, in some embodiments, comprises stimulating the activated synaptic pathway. The importance of achieving activation of the synaptic pathway prior to performance of stimulating step 120 should be noted, because stimulating step 120 acts to potentiate the activated state, but not to cause activation. Stimulating synaptic or brain pathways that have been activated by prior treatment, such as treatment with ketamine or another pharmacologic agent, for example, potentiate the favorable treatment result. Activation of the synaptic pathway, therefore, must be present for stimulating step 120 to have the intended effect of prolonging the relief of symptoms of the neurologic condition by prolonging the time period wherein the synaptic pathway remains activated.

As noted herein, stimulation of the activated synaptic pathway undertaken during stimulating step 120 may be intrinsic (cognitive) stimulation or extrinsic (sensory) stimulation. Intrinsic (cognitive) stimulation is actively initiated by the patient. Extrinsic (sensory) stimulation is passively received through an extrinsic sensory stimulus.

Cognitive stimulation is delivered to the activated synaptic pathway, in some embodiments, by performance of various cognitive exercises commonly known as "brain training" exercises. The exercises include, but are not limited to, daily cognitive exercises performed for a minimum of about thirty (30) minutes to any longer time wherein the patient is able to focus on the activity. Cognitive exercises comprise games and thought-activities designed to increase attention, memory, problem solving, focus, and the like. An example of a cognitive exercise that may be utilized in stimulating step 120 is a proprietary set of exercises known as "Brain HQ®."

A non-limiting example of providing extrinsic stimulation includes placement of a potential voltage difference across the brain. For example, low-voltage direct current devices, such as a transcranial direct-current stimulation device, may be used in some embodiments to provide an extrinsic stimulus to the activated synaptic pathway. The electrodes to create the potential are positioned with a polarity to depolarize the pre and post-synaptic neurons of the synaptic pathway.

Additional examples of providing extrinsic stimulation include placing the brain in a magnetic field. In some embodiments, the extrinsic stimulus comprises a sound. In some embodiments, the extrinsic stimulus comprises light. In some embodiments, the extrinsic stimulus comprises a tactile stimulus, such as a touch or a vibration delivered to an area of the body.

In some embodiments, cognitive stimulation comprises periods of physical aerobic exercise. In some embodiments, the period of exercise is less than about twenty (20) minutes per day. In some embodiments, the period of exercise is between about twenty (20) and about forty-five (45) minutes per day. In some embodiments, the period of exercise is between about forty-five (45) minutes and about one (1) hour per day. In some embodiments, the period of exercise is greater than about one 1) hour per day.

Figure 2:
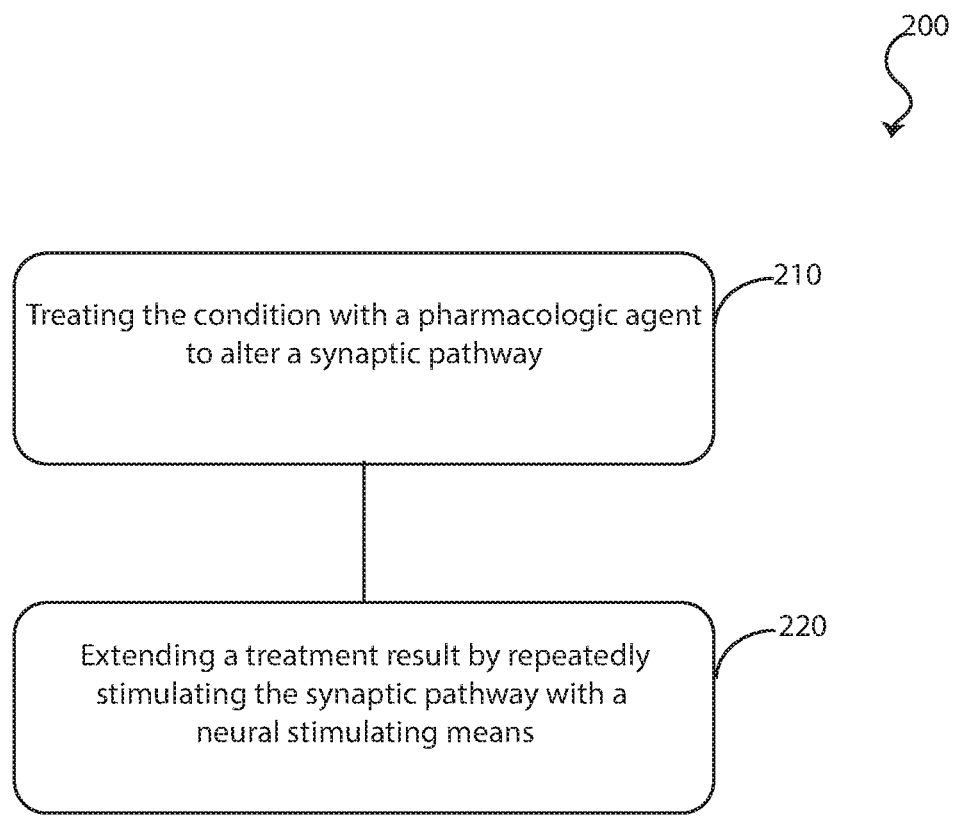
FIG. 2 is a flowchart showing steps of an additional method for treating a neurological condition using synaptic pathway training.

FIG. 2 is a flowchart showing steps of a method for treating a neurologic condition using synaptic pathway training. As shown by FIG. 2, method 200 comprises a treating step 210 and an extending step 220.

Neurologic conditions successfully treated using method 200 include depression (unipolar depression), bipolar depression, mania, and PTSD. Use of method 200 to treat bipolar depression is effective, durable, and does not create any of the side-effects associated with long-term therapy with pharmacologic agents, ECT, or other currently available treatments. Moreover, wherein ketamine is used as the synaptic pathway altering agent, relief from sleep disorders—particularly insomnia—which accompany depression, mania, and PTSD is immediate and persists for months, so long as regular stimulation of the activated synaptic pathway undertaken in the extending step continues. The use of method 200 to treat mania or the manic component of bipolar disease is particularly effective. Currently, treatment of mania requires use of psychotropic medications with a very high incidence of undesirable side effects, including weight gain, increased risk of type-2 diabetes, hypercholesterolemia, dysphoria/apathy from blunted moods, and tardive dyskinesia. Method 200 is dramatically effective for the treatment of mania, in some persons, and none of the aforementioned side effects have been observed.

Method 200 is particularly useful in treating persons with PTSD, for at least three reasons. First, method 200 is an effective treatment for PTSD. Second, initial activation of the synaptic pathway may be accomplished immediately, essentially, during the treating step. Third, means for provision of regular stimulation to the activated synaptic pathway, particularly intrinsic cognitive means, are readily available in field-settings, including some battlefield settings. Use of method 200, therefore, is particularly efficacious for use during deployment, where rapid, simple, and durable treatment of PTSD in a soldier is essential.

Treating step 210, in some embodiments, comprises treating the neurologic condition with a pharmacologic agent to alter a synaptic pathway. The neurologic condition may be depression, bipolar disease, dysthymia, or any number of other neurologic conditions including, but not limited to, those neurologic conditions listed herein. "Treating" means administering one or more therapies over one or more discrete time periods with the intent to either treat the condition, cure the condition, or relieve symptoms caused by the condition. The therapies may comprise: administration of a pharmacologic agent; administration of a treatment, such as ECT or transcranial direct-current stimulation; or the like. Alteration of the synaptic pathway means "activation" of the pathway manifest directly by an increase in synaptic density, or manifest indirectly by relief of improvement of symptoms of the neurologic condition.

Extending step 220, in some embodiments, comprises extending a treatment result by repeatedly stimulating the synaptic pathway with a neural stimulating means. "Extending a treatment result" means causing the favorable results of treatment resulting from treating step 210 to remain manifest for a period of time longer than that period absent extending step 220. In some embodiments, extending step 220 comprises stimulating an activated synaptic pathway with an intrinsic stimulus, as described herein. In some embodiments, extending step 220 comprises stimulating an activated synaptic pathway with ah extrinsic stimulus, as described herein. In some embodiments, extending step 220 comprises performance of physical exercise during recurring periods, such as daily, for a period of days, weeks, or months.

Figure 3:
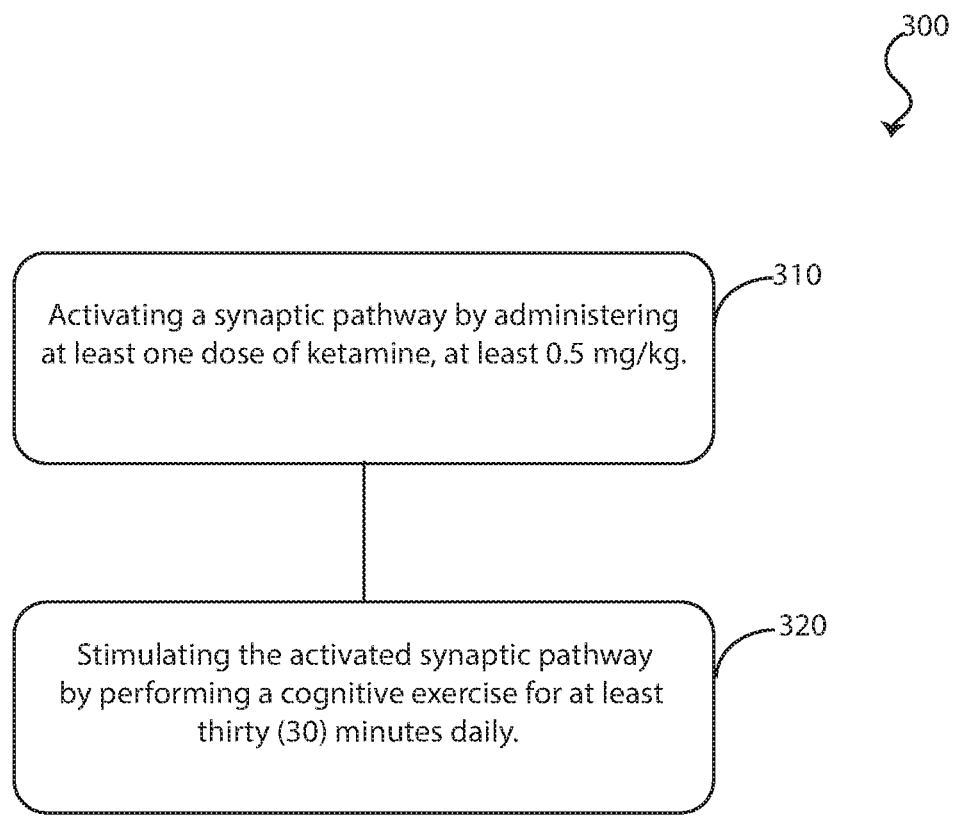
FIG. 3 is a flowchart showing steps of an another method for treating a neuroglial condition using synaptic pathway training.

FIG. 3 is a flowchart showing steps of another method for treating a neurological condition using synaptic pathway training. FIG. 3 shows a method 300 for treating a neurological condition comprising an activating step 310 and a stimulating step 320. In some embodiments, the neurologic condition is depression. In some embodiments, the neurological condition is mania or bipolar disease. In some embodiments, the neurological condition is PTSD.

In some embodiments, activating step 310 comprises activating a synaptic pathway by administering at least one dose of ketamine, at least 0.5 mg/kg. This is a baseline dose, which may need to be repeated one or more times, at intervals of about six (6) days. It is foreseeable that some patients would respond more readily to a higher dose, up to the 1.0 mg/kg dose which is typically used to induce a dissociated state of anesthesia. The dose may need to be repeated two, three, or greater than three times to obtain relief. Relief of symptoms is the clinical marker which indicates activation of the synaptic pathway following completion of activating step 310, prior to performing stimulating step 320.

In some embodiments, stimulating step 320 comprises stimulating the activated synaptic pathway by performing a cognitive exercise for at least thirty (30) minutes each day.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above.

What is claimed is:

1. A method of treating a neurologic condition by synaptic pathway training comprising the steps of:
    activating a synaptic pathway with a pharmacologic agent in an amount in the range of from about 0.5 to about 1 mg/kg; and
    stimulating the activated synaptic pathway.
2. The method of claim 1, wherein the pharmacologic agent comprises an N-methyl-D-aspartate receptor antagonist.

3. The method of claim 1, wherein the pharmacologic agent is a muscarinic receptor antagonist which comprises scopolamine.

4. The method of claim 1, wherein the pharmacologic agent is a member selected from the group of pharmacologic agents consisting of ketamine, Namenda, dextromethorphan, amantadine, dextropropoxyphene, and ketobemidone.

5. The method of claim 1, wherein the pharmacologic agent is a serotonin receptor antagonist which comprises psilocybin.

6. The method of claim 1, wherein the pharmacologic agent is phencyclidine.

7. The method of claim 1, wherein the pharmacologic agent is lysergic acid diethylamide.

8. The method of claim 1, wherein the neurologic condition is depression.

9. The method of claim 1, wherein the neurologic condition is bipolar disorder.

10. The method of claim 1, wherein the neurologic condition is post-traumatic stress disorder.

11. The method of claim 1, wherein stimulating the synaptic pathway comprises performance of a cognitive training exercise.

12. The method of claim 1, wherein the stimulating step comprises exposure of a person to a sensory stimulus.

13. The method of claim 1, wherein the stimulating step comprises applying a magnetic field to a region of a brain.

14. The method of claim 1, wherein the stimulating step comprises applying a potential voltage difference to a region of a brain.

15. A method of enhancing treatment of a neurologic condition comprising the steps of:
   treating the condition with a pharmacologic agent to alter a synaptic pathway; and
   repeatedly stimulating the altered synaptic pathway with a neural stimulating means, wherein the pharmacological agent is not delivered during the stimulating.

16. The method of claim 15, wherein the stimulating of the altered synaptic pathway comprises performance of a cognitive training exercise.

17. The method of claim 15, wherein the stimulating of the altered synaptic pathway comprises providing an external source of stimulation.

18. The method of claim 17, wherein the external source is a magnetic field, a potential voltage difference, or an auditory stimulus.

19. A method of treating a neurologic condition by synaptic pathway training comprising the steps of:
   activating a synaptic pathway by administering at least one dose of ketamine, in an amount in the range of from about 0.5 mg/kg to about 1.0 mg/kg; and
   stimulating the activated synaptic pathway by performing a cognitive training exercise for at least thirty (30) minutes daily.

20. The method of claim 19, wherein the neurologic condition is depression, mania, or post-traumatic stress disorder.

* * * * *